US00PP28440P3

(12) United States Plant Patent
Neumüller

(10) Patent No.: US PP28,440 P3
(45) Date of Patent: Sep. 26, 2017

(54) INTERSPECIFIC PLUM HYBRID ROOTSTOCK NAMED 'DIPREC'

(50) Latin Name: *Prunus domestica×Prunus cerasifera*
Varietal Denomination: DIPREC

(71) Applicant: Michael Neumüller, Hallbergmoos (DE)

(72) Inventor: Michael Neumüller, Hallbergmoos (DE)

( * ) Notice: Subject to any disclaimer, the term of this patent is extended or adjusted under 35 U.S.C. 154(b) by 0 days.

(21) Appl. No.: 14/757,289

(22) Filed: Dec. 10, 2015

(65) Prior Publication Data

US 2017/0172030 P1 Jun. 15, 2017

(51) Int. Cl.
*A01H 5/08* (2006.01)

(52) U.S. Cl.
USPC ..... Plt./180

(58) Field of Classification Search
USPC ..... Plt./180
See application file for complete search history.

*Primary Examiner* — Annette Para
(74) *Attorney, Agent, or Firm* — Ballew Law

(57) ABSTRACT

A new interspecific plum hybrid rootstock named 'DIPREC' is disclosed. 'DIPREC' exhibits a resistance to Plum Pox Virus (PPV) mediated by a hypersensitive response to PPV. 'DIPREC' is used as a rootstock for commercial fruit trees. This new and distinct *prunus domestica×prunus cerasifera* plant can be used as a rootstock for varieties of plum and other *prunus* species that exhibits desirable propagation characteristics, resistance to Plum Pox Virus and shows white flowers.

6 Drawing Sheets

Genus and species: *Prunus domestica×Prunus cerasifera*.
Variety denomination: 'DIPREC'.

CROSS-REFERENCE TO RELATED APPLICATIONS

None

STATEMENT REGARDING FEDERALLY SPONSORED RESEARCH OR DEVELOPMENT

None

BACKGROUND OF THE INVENTION

'DIPREC' is a product of a controlled breeding program carried out by the inventor in Hallbergmoos, Germany. 'DIPREC' is an interspecific plum hybrid rootstock that resulted from a cross between *Prunus domestica* clone 'Hoh 6482' (female parent, unpatented) and *Prunus cerasifera* 'Spate Myrobalane' (male parent, unpatented). There is no similarity to known rootstock varieties used for *Prunus domestica*. The purpose of breeding 'DIPREC' was to obtain a *Prunus* rootstock with full resistance to Sharka disease caused by the Plum Pox Virus (PPV) inducing precocity, good fruit size and medium tree size. The following characteristics distinguish 'DIPREC' from other varieties known to the breeder: the morphology is intermediate between European plum and Myrobalane; easy to propagate by cuttings and in vitro; resistant to several isolates of Plum Pox Virus (PPV), amongst them isolates of PPV-D, PPV-Rec, PPV-M, PPV-EA, and PPV-W. Trees of 'DIPREC' can easily be distinguished from their parent varieties: Fruits of 'DIPREC' are violet and ripen mid of August, those of 'Hoh 6482' are blue and ripen mid of July. Fruits of 'Spate Myrobalane' are yellow and ripen in September. When a PPV infected scion is grafted onto a 'DIPREC' rootstock plant, the scion part will either not grow or die off within a few months after bud break. Therefore, no latently PPV infected plant can leave the nursery. In that way, 'DIPREC' can help to slow down the process of spreading PPV.

BRIEF DESCRIPTION OF THE PHOTOGRAPH

Figure 1:
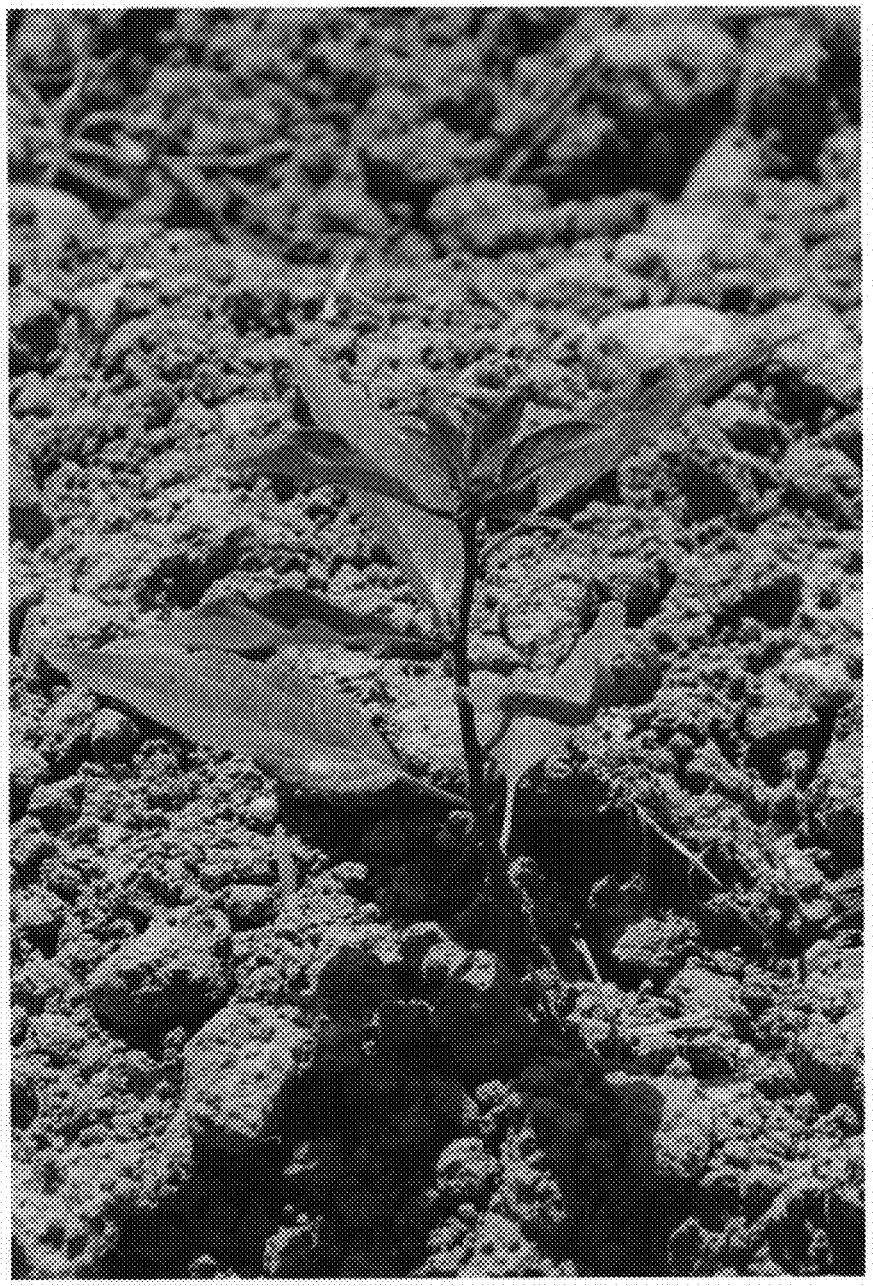
FIG. 1 illustrates an immature 'DIPREC' rootstock plant.
Figure 2:
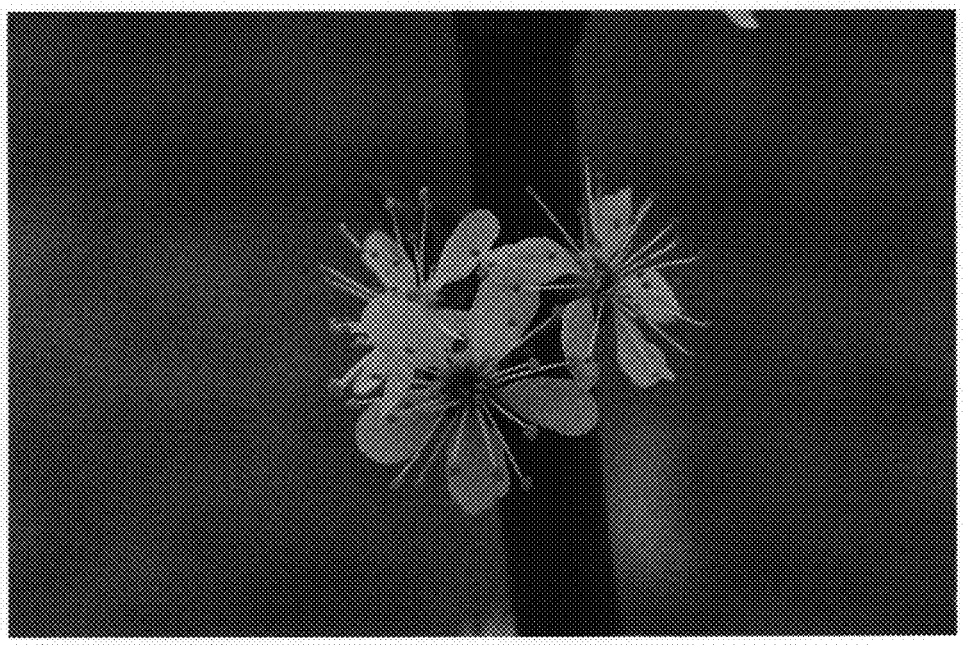
FIG. 2 illustrates flowers of a mature 'DIPREC' rootstock plant.
Figure 3:
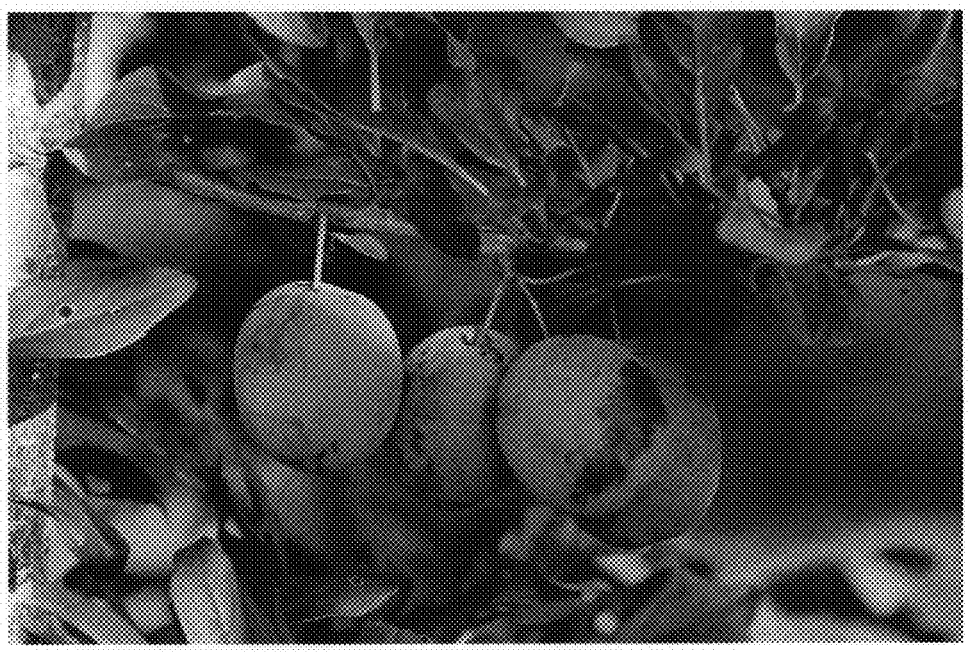
FIG. 3 illustrates fruit on a mature 'DIPREC' rootstock plant.
Figure 4:
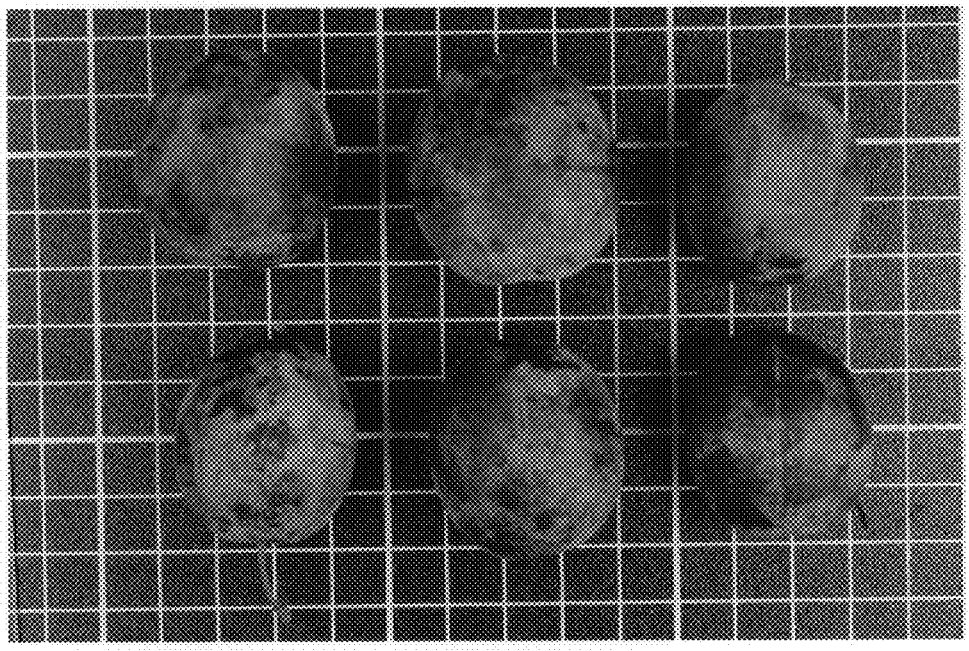
FIG. 4 illustrates fruit produced from a mature 'DIPREC' plant.
Figure 5:
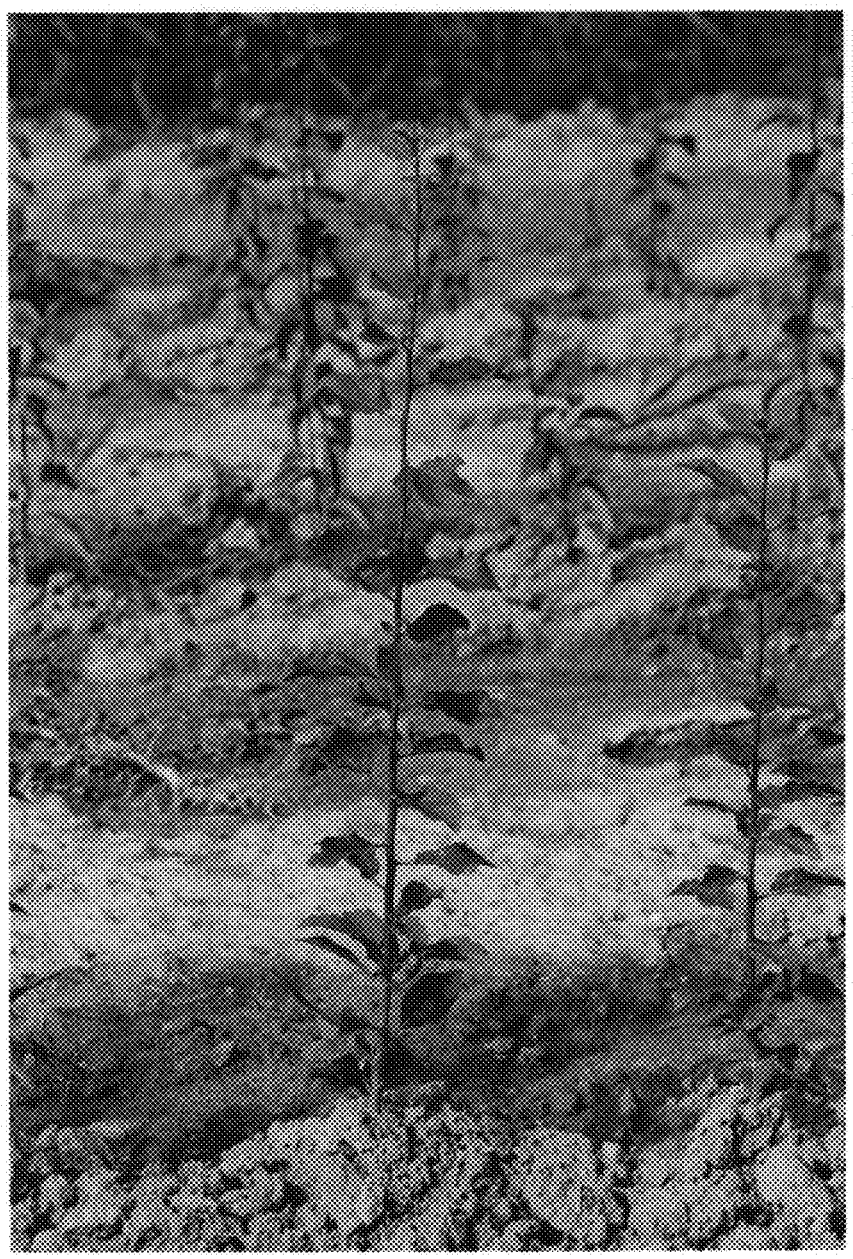
FIG. 5 illustrates one year old shoots of 'DIPREC' rootstock plant.
Figure 6:
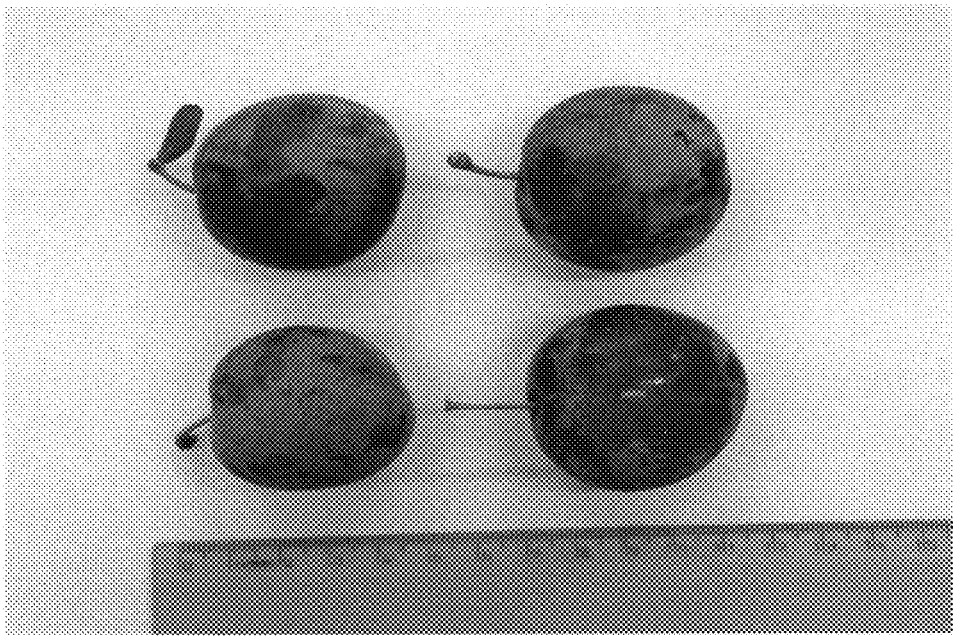
FIG. 6 illustrates size of fruit produced from a mature 'DIPREC' plant.

The colors of these illustrations may vary with lighting conditions and, therefore, color characteristics of this new variety should be determined with reference to the observations described herein, rather than from these illustrations alone.

DETAILED BOTANICAL DESCRIPTION

The data which defines these characteristics were collected by asexual reproductions via cuttings. The plants were grown at Freising-Weihenstephan, Bavaria, Germany, under standard European plum growing conditions outdoors in Germany. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants, of the new variety may vary from the stated average. The color readings were taken in natural daylight and the plant was ten years old when described. All color references are based on The 1995 Royal Horticultural Society Colour Chart of The Royal Horticultural Society of London.

Use: Rootstock for commercial fruit trees.

Tree:

*Size*.—Height: 2.8 m.

*Size*.—Spread: 2.5 m.

*Vigor*.—Medium.

*Form*.—Spherical.

*Bearing*.—Regular high fruit set.

*Density*.—Medium.

*Pathogen resistance*.—Fungal resistance: Stable. Insects: Normal susceptibility to leaf insects. Mites: Moderately tolerant. Viruses — Resistant to Plum Pox Virus (PPV) by hypersensitivity resistance. Other diseases: Tolerant to bacterial disease.

Rootstock performance:

*Root sprouts* (*suckering*).—Few.

*Anchorage*.—Very well.

*Compatibility*.—Very good with *Prunus domestica, Prunus cerasifera, Prunus salicina*, good with *Prunus armeniaca.*

*Vigour*.—Medium.

Trunk:

*Size*.—12 cm at approximately 30 cm from the ground.

*Bark color*.—N199A.

*Surface texture*.—Smooth.

*Lenticels*.—Length: 1.5 cm. Color: 163A. Density: Medium.

Branches:

*Diameter*.—0.8 cm.

*Surface texture*.—Smooth, no pubescence present.

*Color*.—199A.

*Average angle*.—31°.

*Lenticels*.—Length: 0.3 cm. Width: 0.8 cm. Density: Medium. Color: 163A. Shape: Small and unremarkable on young branches.

Leaves:

*Length*.—6.5 cm.

*Width*.—3.2 cm.

*Form*.—Lanceolate — elliptic.

*Base*.—Attenuate.

*Apex*.—Acute.

*Margin*.—Crenate — serrulate.

*Pubescence*.—Upper surface: Almost absent. Lower surface: Almost absent.

*Color*.—Young Leaves: Upper surface: 141D. Lower surface: 146C. Old leaves: Upper surface: 131D. Lower surface: N134D.

*Petiole*.—Length: 1.8 cm. Color: Upper surface: 181A. Lower surface: 181A.

*Veins*.—Venation type: pinnate. Color: Upper surface: 131D. Lower surface: N134D.

Flower buds:

*First bud burst*.—Approximately early or mid-April in Freising, but varies by region.

*Pedicel*.—Length: 1.5 cm. Color: N155.

*Bud*.—Length: 0.5 cm. Width: 0.2 cm. Color: N199C.

Flowers:

*Blooming period*.—$10^{th}$-$20^{th}$ of April in Freising.

*Pollination requirements*.—Autofertile.

*Number of flowers per raceme*.—1-3, mostly 2.

*Fragrance*.—Weak.

*Petals*.—Number: 5, alternatively arrange to sepals. Length: 9.2 mm. Width: 6.4 mm. Form: elliptic. Color: N999D.

*Sepals*.—Number: 5, alternatively arranged to sepals. Length: 3.5 mm. Width: 1.7 mm. Form: Ensiform. Color: 137C.

*Stamen*.—Average number per flower: 21.

*Anthers*.—Color: 14A.

*Pistils*.—One per flower.

*Style*.—Length: Medium.

Fruit: Fruits ripen in late August in Germany.

*Size*.—Small.

*Skin*.—Thickness: Fine.

*Texture*.—Soft.

*Color*.—83B.

*Seeds*.—1 per fruit.

*Stem*.—Length: 1.8 cm. Width: 1.8 mm.

Vigour: European plum trees grafted onto 'DIPREC' rootstock show medium vigour, similar to 'Ishtara' or 'St. Julien A'.

Multiplication ability: The new variety may be multiplied by hardwood cuttings, softwood cuttings and micropropagation.

What is claimed is:

1. A new and distinct interspecific plum hybrid rootstock as shown and described herein.

* * * * *